United States Patent [19]
Harata et al.

[11] Patent Number: 5,092,676
[45] Date of Patent: Mar. 3, 1992

[54] METHOD AND SYSTEM FOR EVALUATING GLOSS AND BRIGHTNESS CHARACTER OF COATED PAINT FILM

[75] Inventors: Hiroaki Harata; Mitsuo Hashimoto; Hiroshi Tabata, all of Yokohama, Japan

[73] Assignee: Nissan Motor Co., Ltd., Japan

[21] Appl. No.: 506,189

[22] Filed: Apr. 9, 1990

[30] Foreign Application Priority Data

Apr. 13, 1989 [JP] Japan .................................. 1-91729

[51] Int. Cl.$^5$ .............................................. G01B 11/30
[52] U.S. Cl. ..................................... 356/371; 356/446; 356/124.5
[58] Field of Search ............... 356/371, 124.5, 445–448

[56] References Cited

U.S. PATENT DOCUMENTS 4,846,578  7/1989  Morita et al. ...................... 356/446

FOREIGN PATENT DOCUMENTS

16-19039   9/1941  Japan .
52-138960 11/1977  Japan .
59-27207   2/1984  Japan .
62-103545  5/1987  Japan .
62-233712 10/1987  Japan .

Primary Examiner—Richard A. Rosenberger
Assistant Examiner—Hoa Pham
Attorney, Agent, or Firm—Leydig, Voit & Mayer

[57] ABSTRACT

A method for evaluating a gloss and brightness character of a coated paint film. The idea of the gloss and brightness character is classified into three feelings, i.e., a smooth feeling, a thickness feeling and a gloss feeling. Three frequency regions for the respective three feelings are selected to be in well correlation to organoleptic values which are for the respective three feelings. In the evaluating method, the degree of a surface roughness of the coated paint film is converted into frequency components. Then the frequency regions are abstracted from the frequency components. The frequency regions are numerically estimated. Finally, the gloss and brightness character of the coated paint film is evaluated in accordance with the numerically estimated frequency regions.

4 Claims, 6 Drawing Sheets

GLOSS AND BRIGHTNESS CHARACTER VALUE

FIG. 7
*PRIOR ART*

METHOD AND SYSTEM FOR EVALUATING GLOSS AND BRIGHTNESS CHARACTER OF COATED PAINT FILM

BACKGROUND OF THE INVENTION

1. Field of the Invention

This invention relates to a method and system for evaluating a gloss and brightness character of a coated paint film, and more particularly to such a method and system for obtaining a numerically estimated total evaluation value for the gloss and brightness character which value is in good correlation to an organoleptic value for the gloss and brightness character.

2. Description of the Prior Art

Figure 1:
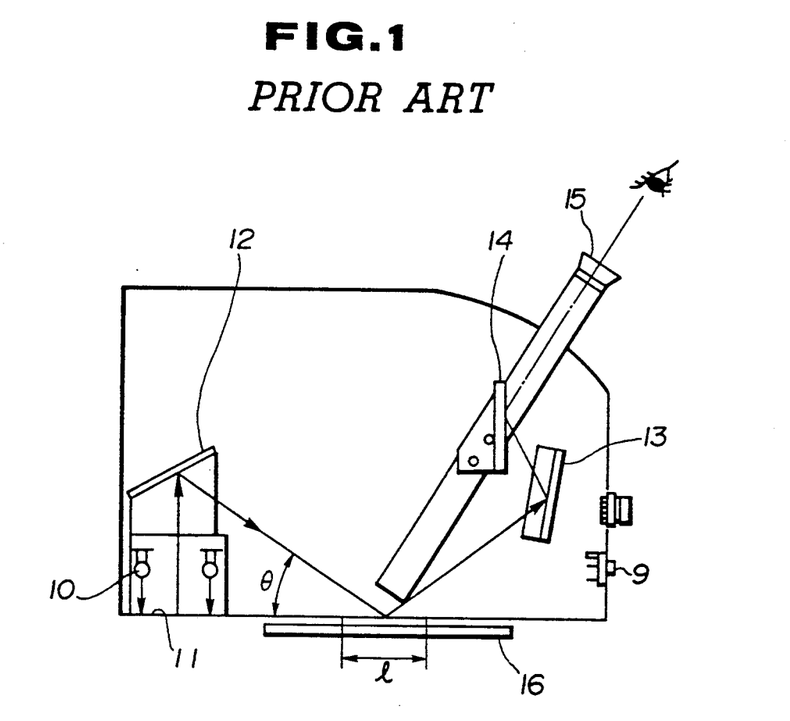
FIG. 1 is an explanatory side view of a conventional method and device for evaluating a gloss and brightness character of a coated paint film.

Hitherto, evaluation of a gloss and brightness character of a coated paint film has been usually accomplished by using a device which mainly functions organoleptically under eye observation, as disclosed for example in a Japanese Utility Model Publication No. 41-19039. An example of such a gloss and brightness evaluation device will be illustrated with reference to FIG. 1. In this evaluation device, when a switch 9 is turned on, a light bulb 10 is lighted to lighten a test pattern 11. Then light from the test pattern 11 is reflected by mirrors 12, 13, 14 and enters an eye glass 15. Thus, the reflected image of the test pattern 11 is observed by an observer whose eye only is shown in FIG. 1. As shown, a specimen plate 16 coated with a paint film is put in a light path from the test pattern 11 to the eye glass 15. The entry angle $\theta$ of light to the paint-coated specimen plate is 35 degrees, and the length l of a range in which the light enters is 50 mm.

Observation is accomplished by looking the image of the test pattern 11 through the eye glass 15. The gloss and brightness character is evaluated from deformation of the image of the test pattern 11. The test pattern 11 is provided with aligned large to small letters. The gloss and brightness of the coated paint film are higher as the smaller letters can be read by the observer.

The thus arranged gloss and brightness character evaluation device is arranged to evaluate the gloss and brightness of the coated paint film depending upon capability of reading the letters in the test pattern. Accordingly, the gloss and brightness character evaluation device has the following disadvantages:

(1) The observation result is unavoidably largely affected by the visual acuity of the observer. In other words, the observation result is largely affected by the deterioration degree in eye-ball focal distance control function which usually deteriorates with the observer's ages over 20 years old. The influence of such a deteriorated focal distance control function cannot be covered.

(2) The smoothness feeling and the gloss feelings as constituting elements of the gloss and brightness character can be totally evaluated but cannot be independently evaluated.

(3) The thickness feeling as an important constituting element of the gloss and brightness character cannot be evaluted.

(4) In case the surface condition of the coated paint film is considerably good, distinction in surface condition becomes difficult so as to provide the same evaluation value even among different samples.

In view of the above, establishment of the gloss and brightness evaluation method correlating well to visual observation has been eagerly desired.

Figure 2:
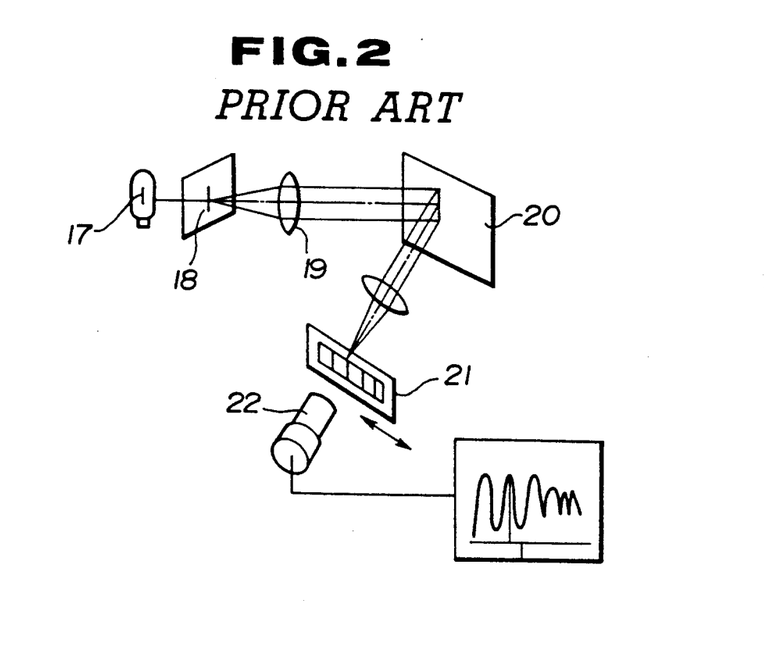
FIG. 2 is an explanatory perspective view of another conventional method and device for evaluating the gloss and brightness character of the coated paint film.

Under such circumstances, it has been proposed to evaluate the gloss and brightness character of the coated paint film without depending upon visual observation and by using a gloss and brightness measuring device which is for example disclosed in Japanese Patent Provisional Publication No. 52-138960. The gloss and brightness character measuring device is illustrated with reference to FIG. 2. In this device, incidence of parallel beam of light is made to impinge on the surface of an object 20 to be measured at an entry angle of 45 or 60 degrees, under the effect of an optical system including a light source 17, a slit 18 and a lens 19. The light beam is reflected on the surface of the object 20 and scattered in accordance with the surface roughness condition of the object 20. The reflected and scattered light beam is concentrated on the surface of a pattern 21 and measured optically in degree of brightness by using a light receiving device 22, thus obtaining a gloss and brightness character value C which is given by the following equation:

$$C = \frac{M - m}{M + m} \times 100(\%)$$

where M is the maximum value of tranmitted light in a lighted part of the pattern 21; m is the minimum value of the transmitted light in a dark part of the pattern 21.

However, with such a gloss and brightness character measuring device, the constituting elements of the gloss and brightness character cannot be independently evaluated. As a result, appropriate and desirable evaluation cannot be made in case the constituting elements of the gloss and brightness character are different among objects or in case concepts to be expressed are different among objects, i.e., when the thickness feeling and/or the smoothness feeling are particularly emphasized.

SUMMARY OF THE INVENTION

In view of the above disadvantages of the conventional gloss and brightness character evaluation methods, the inventors have discovered that the gloss and brightness character of the coated paint film expressed as a human's organoleptic amount is an idea which is constituted by combining some different feelings (textures) representing the surface roughness condition of the coated paint film, in the course of research and development for an evaluating method of the gloss and brightness character. Then the inventors have reached a knowledge in which the total evaluation value of the gloss and brightness character of the coated paint film to correlates well with to an organoleptic value which is observed by visual observation, by independently numerically estimating the above-mentioned different feelings (textures) and by defining the gloss and brightness character as a composite function of them. In this connection, the gloss and brightness character of the coated paint film is referred to as a degree at which the image of an object is reflected on the surface of a coated paint film, according to Japanese Industrial Standard.

Therefore, it is an object of the present invention to provide an improved gloss and brightness character evaluation method and system which provide a total evaluation value correlating well with a corresponding organoleptic value by visual observation.

Another object of the present invention is to provide an improved gloss and brightness character evaluation method and system which can independently evaluate the constituents of a gloss and brightness character of a coated paint film.

A further object of the present invention is to provide an improved gloss and brightness evaluation character method and system in which a gloss and brightness character is classified into a plurality of factors or feelings, upon which a total evaluation value of the gloss and brightness is obtained in accordance with the factors which are numerically estimated.

An aspect of the present invention resides in a method for evaluating the gloss and brightness character of a coated paint film. The method comprises the following steps in the order named: (1) converting the degree of a surface roughness of the coated paint film into frequency components; (2) abstracting a plurality of frequency regions from the frequency components, the frequency regions respectively corresponding to factors representing the gloss and brightness character of the coated paint film; (3) numerically estimating the frequency regions; and (4) evaluating the gloss and brightness character of the coated paint film in accordance with the numerically estimated frequency regions.

Another aspect of the present invention resides in a system for evaluating the gloss and brightness character of the coated paint film. The system comprises a first device for converting the degree of a surface roughness of the coated paint film into frequency components. A second device is provided to abstract a plurality of frequency regions from the frequency components. The frequency regions respectively correspond to a plurality of factors representing the gloss and brightness of the coated paint film. A third device is provided to numerically estimating the frequency regions. Additionally, a fourth device is provided to evaluate the gloss and brightness character of the coated paint film in accordance with the numerically estimated frequency regions.

DETAILED DESCRIPTION OF THE INVENTION

Figure 3:
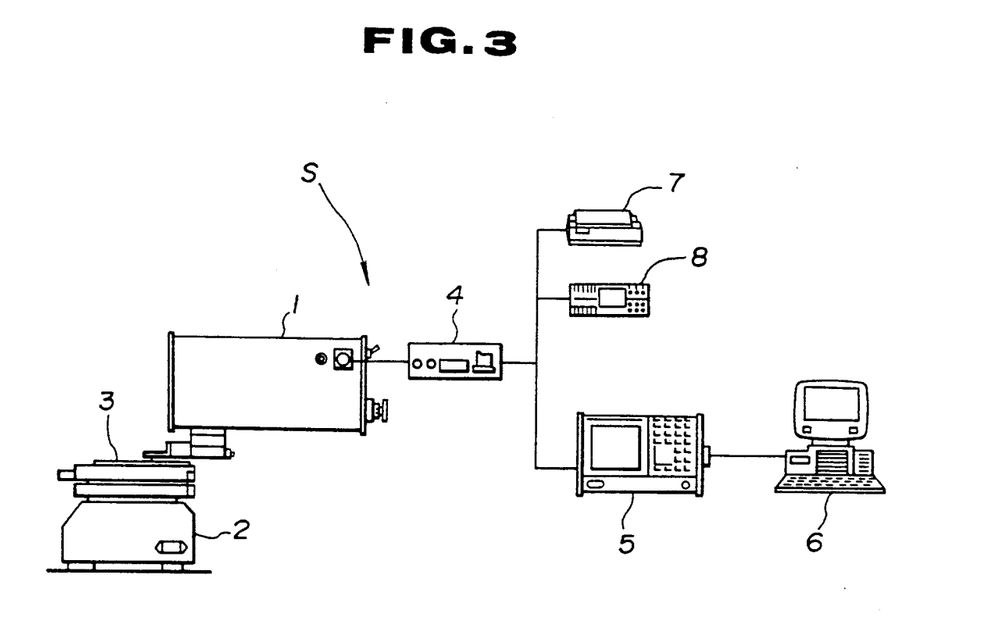
FIG. 3 is an explanatory view of a system for evaluating the gloss and brightness character of a coated paint film, to which an evaluating method according to the present invention is applied.

Referring now to FIG. 3, there is shown an example of a system S for evaluating a character gloss and brightness character of a paint film coated on a member such as a steel plate. The gloss and brightness character represents a texture or surface condition of the coated paint film. With this system S, a gloss and brightness character evaluation method according to the present invention is carried out as discussed hereinafter.

The gloss and brightness character evaluation system S comprises a surface roughness tester 1 which is of a so-called needle contacting type wherein a measuring needle is in contact with the surface of a coated paint film. More specifically, a diamond needle (measuring needle) sweeps the surface of the coated paint film at a constant speed thereby to convert the vertical movement of the needle due to the roughness of the surface of the coated paint film into a voltage wave form in terms of time lapse. It will be understood that the surface roughness tester 1 may be replaced with one which is not of the needle contacting type and is of a so-called optical type wherein the surface roughness of the coated paint film is optically detected. Such optical type surface roughness tester is disclosed, for example, in Japanese Patent Provisional Publication Nos. 59-27207, 62-103545 and 62-233712.

As shown, the diamond needle of the surface roughness tester 1 is in movable contact with the surface of a sample 3 in which a paint film is coated on the surface of a steel plate. The surface roughness tester 1 is mounted on a vibration proof mount 2 to absorb vibration of a measuring system (not identified) including the surface roughness tester 1. A controller 4 is electrically connected to the surface roughness tester 1 to control operation of the surface roughness tester 1.

A Fourier transformation device 5 is electrically connected to the controller 4 and arranged to convert the voltage waveform from the measuring system into frequency components. More specifically, the Fourier transformation device 5 makes an analog-to-digital convertion in which an analog signal from the surface roughness tester 1 is converted into a digital signal. Additionally, the device 5 has a function to make a frequency analysis by Fourier transformation thereby to numerically estimate as a power spectrum the surface roughness represented by each frequency component. The value of the power spectrum is represented in terms of wave length or frequency, in which the power spectrum value is proportional to the square of the surface roughness or the amplitude of vertical movement of the diamond needle of the surface roughness tester 1. The Fourier transformation device may be replaced with a device including a high-pass filter or a low-pass filter to obtain necessary frequencies. In this case, the surface roughness represented by the wave form passed through a frequency filter can be numerically estimated by a known idea such as a center line average height.

A computer 6 is electrically connected to the Fourier transformation device 5 and arranged to analyze data which is obtained as a result of the Fourier transformation or frequency analysis. More specifically, the computer 6 executes calculation such as accumulation (integration) or accumulation after weighting, regarding the power spectrums in each of three frequency (wavelength) ranges which respectively correspond to three texture feelings of the coated paint film, i.e., a smoothness feeling, a thickness feeling and a gloss feeling. It is to be noted that the inventors have found that an effective evaluation of the coated paint film is accomplished by classifying the texture feeling of the coated paint film into the above-mentioned three feelings and abstracting or selecting the above-mentioned three frequency ranges which respectively correspond to the three feelings. Such abstracting was made on the basis of experimental data as discussed after.

Here, it may be preferable to make a pretreatment calculation such as square root conversion or logarithm conversion before the above-mentioned accumulation in case of treating parameters such as the power spectrum (an amount proportional to the square of the amplitude) which lacks linearity relative to an organoleptic values.

Furthermore, weighting is made to each of accumulated (power spectrum) values which are respectively corresponding to the three feelings and obtained by the above calculation (accumulation). Then, the thus weighted respective values are totalled thus to obtain a total evaluation value of the gloss and brightness character of the coated paint film. A platter 7 is provided to be electrically connected to the controler 4 for the purpose of drawings a chart corresponding to the surface roughness measured by the surface roughness tester 1. Additionally, a printer 8 is electrically connected to the controller 4 to print the data measured by the surface roughness tester 1.

Figure 4:
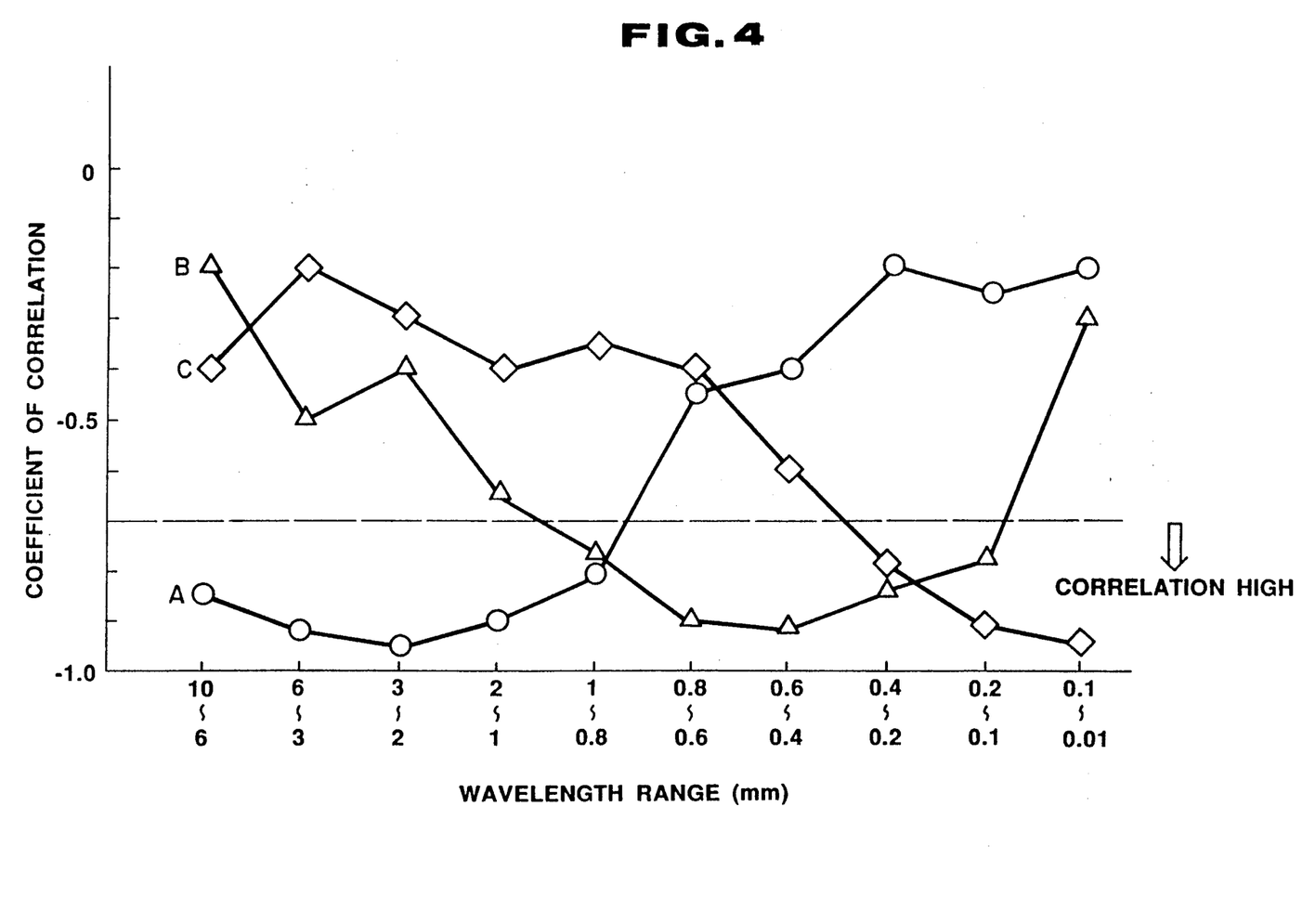
FIG. 4 is a graph showing the relationship between a wavelength range and a coefficient of correlation (to an organoleptic value) with regard to three feelings (a smoothness feeling, a thickness feeling and a gloss feeling)

FIG. 4 shows data by which the above-mentioned three wavelength (frequency) ranges corresponding to the three feelings (the smooth feeling, the thickness feeling and the gloss feeling) of the coated paint film were determined or selected. In FIG. 4, a line a indicates the accumulated values of power spectrums in the smooth feeling; a line b indicates those in the thickness feeling; and a line c indicates those in the gloss feeling. As shown, a correlation is determined between a numerically estimated organoleptic value for each of the three feelings of the coated paint film and an accumulated value of power spectrums within each wavelength (frequency) range indicated on the axis of abscissa of the graph of FIG. 4 thereby obtaining a coefficient of correlation as indicated on the axis of ordinate of the graph. The numerically estimated organoleptic value is obtained by using a so-called paired comparison test under visual observation. With reference to the graph of FIG. 4, a wavelength (frequency) region in which a coefficient of correlation is higher than a predetermined (absolute) value (0.7) was determined to correspond to each of the three feelings (the smoothness feeling, the thickness feeling and the gloss feeling). The predetermined (absolute) value of the coefficient of correlation may be 0.8. Thus, it will be seen from the graph of FIG. 4, that the smoothness feeling corresponds to the wavelength region not lower than 0.8 mm preferably from 1.0 to 10 mm; the thickness feeling corresponds to the wavelength region from 0.1 to 1.0 mm preferably from 0.8 to 0.2 mm; and the gloss feeling corresponds to the wavelength region not higher than 0.4 mm preferably not higher than 0.2 mm.

Figure 5A:
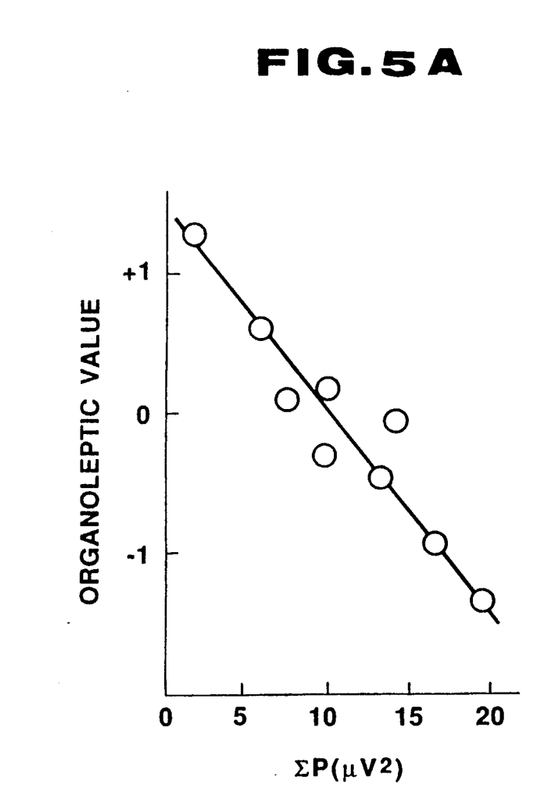
FIGS. 5A, 5B and 5C are graphs which respectively show the relationships each between an organoleptic value and an accumulated value of power spectrums within a wavelength region representing each feeling in FIG. 4, with respect to the three feelings of FIG. 4.
Figure 5B:
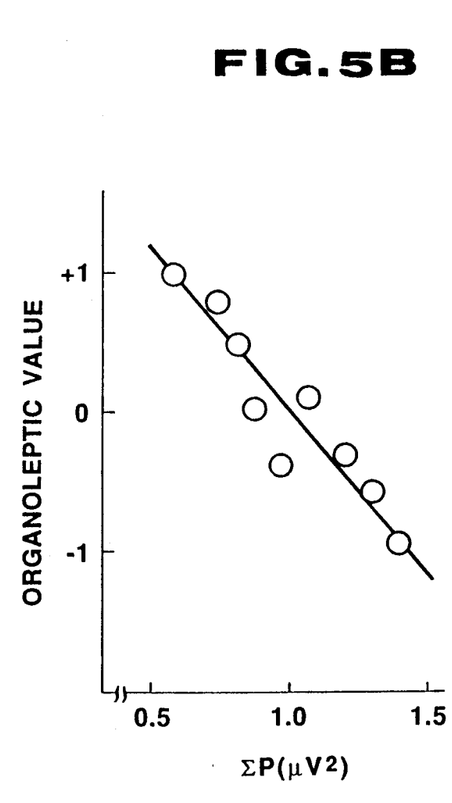
Figure 5C:
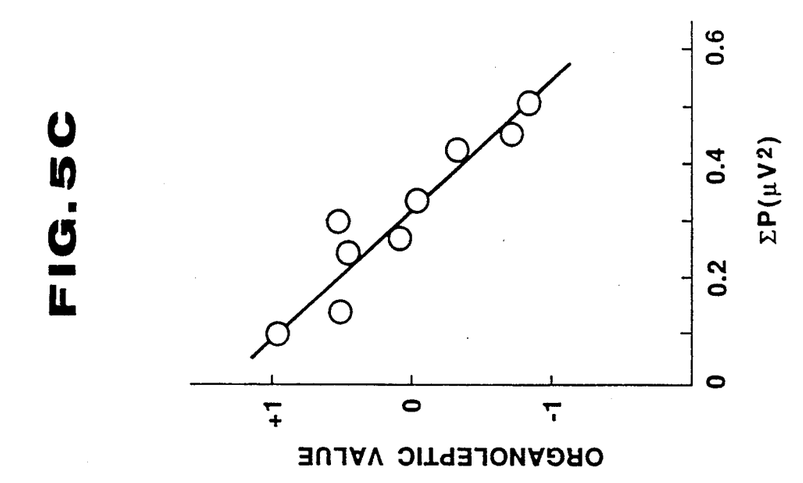

FIGS. 5A to 5C show a relationship between the numerically estimated organoleptic value and the accumulated value $\Sigma P(\mu V^2)$ of the power spectrums within each of the above three wavelength regions which respectively correspond to the smoothness feeling, the thickness feeling and the gloss feeling. Of these, FIG. 5A represents the relationship of the smoothness feeling; FIG. 5B represents the relationship of the thickness feeling; and FIG. 5C represents the relationship of the gloss feeling. These figures demonstrate that the numerically estimated organoleptic value and the accumulated value of power spectrums are in a linear relationship with respect to the smooth feeling, the thickness feeling and the gloss feeling.

Figure 6:
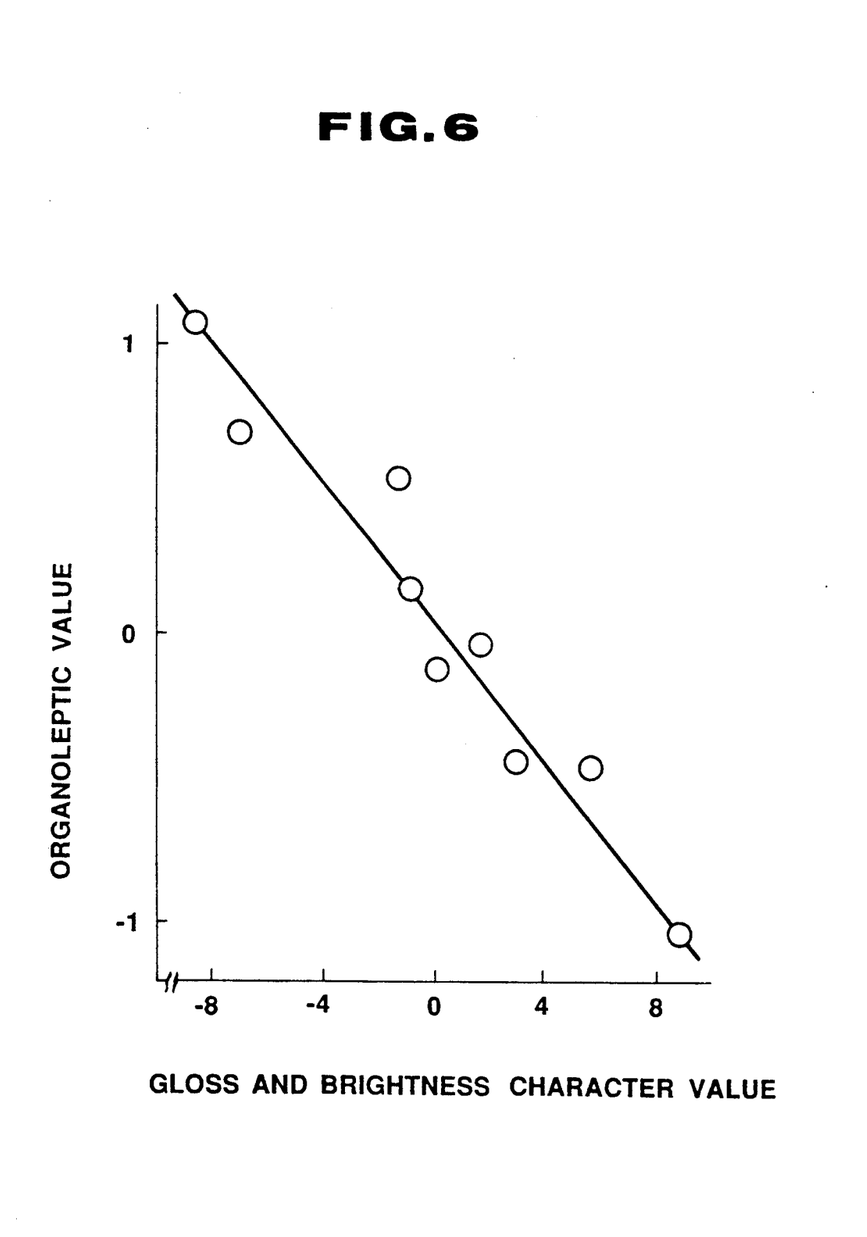
FIG. 6 is a graph showing the relationship between a total evaluation value of the gloss and brightness character of the coated paint film according to the system of FIG. 3 and an organoleptic value.

FIG. 6 shows a relationship between the numerically estimated organoleptic value of the texture of the coated paint film and a total evaluation value of a gloss and brightness character value of the coated paint film. The total evaluation value is obtained by totalling the accumulated values within the respective wavelength regions corresponding to the three feelings (the smooth feeling, the thickness feeling and the gloss feeling) upon undergoing weighting calculation. Standardizing is carried out to compare the accumulated values in the same level or scale, before the weighting calculation. The weighting calculation is made with a ratio of coefficients of 3 (the smoothness feeling): 2 (the thickness feeling): 1 (the gloss feeling). It will be understood that in order to obtain the desirable total evaluation value, it is may be possible to use any other weighting and/or any operator. For example, an operation expression which is high in correlation between the organoleptic value and the total evaluation value may be obtained by a multi-regression analysis in which the total evaluation value is estimated from the accumulated values of the power spectrums respectively corresponding to the three feelings. The data of FIG. 6 demonstrates that the gloss and brightness character values obtained according to the present invention is correlates well with the organoleptic values.

Figure 7:
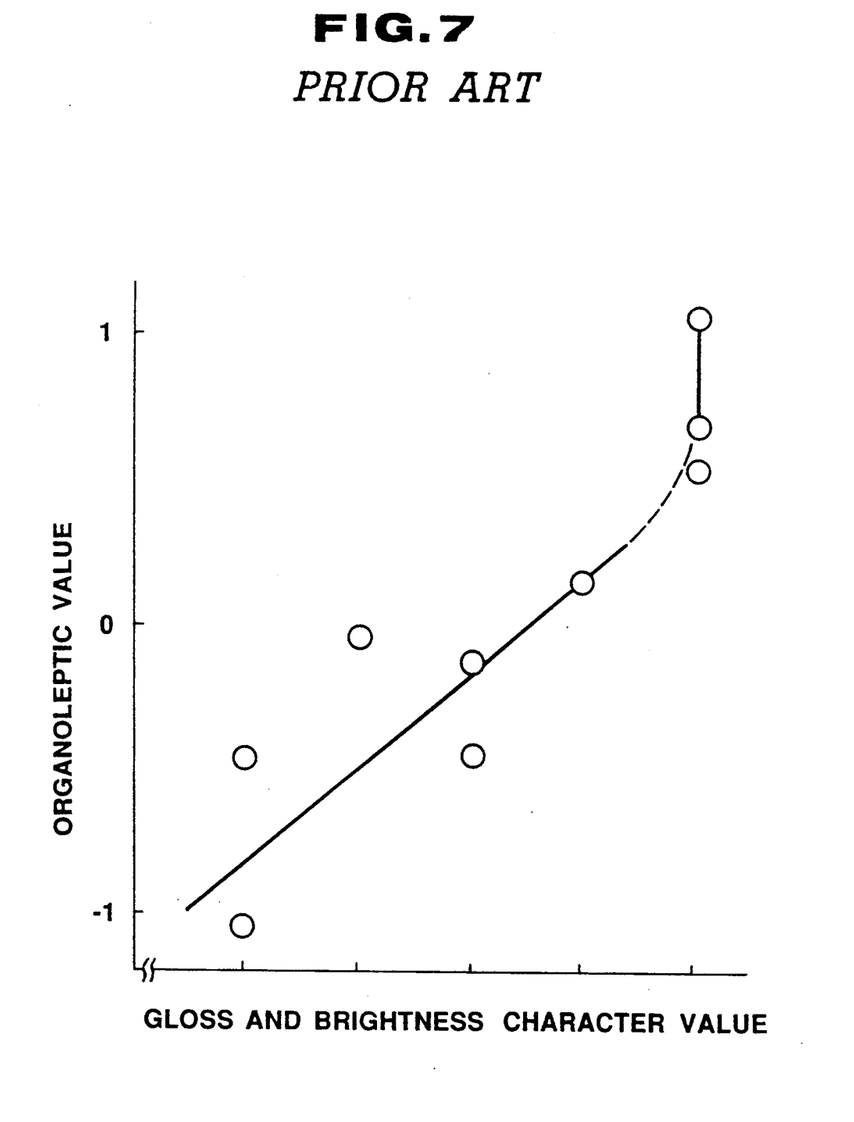
FIG. 7 is a graph showing the relationship between a measured value according to the device of FIG. 2 and an organoleptic value.

FIG. 7 shows a relationship between a numerically estimated organoleptic value (obtained under visual observation) of the texture of a coated paint film and the gloss and brightness character value measured by the conventional gloss and brightness character evaluation device shown in FIG. 1. The graph of FIG. 7 is provided for the purpose of comparison with the graph of FIG. 6 in connection with the present invention.

It will be seen from the graph, that there is a considerable scattering in the relationship between the organoleptic value and the measured value. Besides, the same measured value comes out even if the organoleptic values are considerably different, in case the surface condition of the coated paint film is relatively good. These demonstrates that the gloss and brightness character values measured by the device of FIG. 1 do not correlate well with the organoleptic value.

What is claimed is:

1. A method for evaluating a gloss and brightness character of a coated paint film, comprising:
    converting degree of a surface roughness of the coated paint film into a plurality of frequency components;
    abstracting a plurality of frequency regions from the frequency components, said frequency regions respectively corresponding to factors representing the gloss and brightness character of the coated paint film, said factors including a smoothness feeling, a thickness feeling and a gloss feeling of the coated paint film and said frequency regions including first, second and third frequency regions which respectively represent the smoothness, thickness and gloss feelings, wherein said first, second and third frequency regions respectively correspond to a first wavelength region not lower than 0.8 mm, a second wavelength region between 0.1 to 1.0 mm and a third wavelength region not higher than 0.4 mm;

numerically estimating respectively said frequency regions; and evaluating the gloss and brightness character of the coated paint film in accordance with said numerically estimated frequency regions.

2. A method as claimed in claim 1, wherein said first wavelength region is between 1.0 to 10 mm.

3. A method as claimed in claim 1, wherein said second wavelength region is between 0.8 to 0.2 mm.

4. A method as claimed is claim 1, wherein said third wavelength region is not higher than 0.2 mm.

* * * * *